United States Patent [19]

Beach

[11] 4,084,937
[45] Apr. 18, 1978

[54] RECEPTACLE FOR COLLECTING URINE SAMPLES

[76] Inventor: Janet Beach, Box 904, Camden, Me. 04843

[21] Appl. No.: 745,090

[22] Filed: Nov. 26, 1976

[51] Int. Cl.² .................. B01L 3/00; E03D 13/00; G01N 1/18
[52] U.S. Cl. ..................... 23/259; 4/113.1; 4/144.1; 73/421 R; 128/2 F; 220/20
[58] Field of Search ............ 229/15; 4/110; 23/259, 23/292; 128/2 F, 295; 220/20, 22; 210/513, 521; 209/18, 447, 453, 454, 485; 73/421 R, 425.4 R

[56] References Cited

U.S. PATENT DOCUMENTS

| | | | |
|---|---|---|---|
| 2,321,660 | 6/1943 | Courtney | 229/15 |
| 2,447,425 | 8/1948 | Norton et al. | 210/513 X |
| 2,575,768 | 11/1951 | Pearsall | 210/513 X |
| 3,263,803 | 8/1966 | Almond | 220/22 X |
| 3,722,503 | 3/1973 | Hovick | 4/110 X |
| 3,933,654 | 1/1976 | Middelbeek | 210/521 |

*Primary Examiner*—Morris O. Wolk
*Assistant Examiner*—Roger F. Phillips
*Attorney, Agent, or Firm*—William G. Rhines

[57] ABSTRACT

This invention relates to Medical Apparatus, and in one embodiment useful as a urine sampling receptacle wherein urine initially discharged therein may be segregated in order to get a sample which is more nearly representative in chemical composition, comprising a sloped false bottom having an aperture therethrough which includes at least a portion of one edge thereof and is positioned at the bottom of the slope.

3 Claims, 11 Drawing Figures

U.S. Patent  April 18, 1978  4,084,937
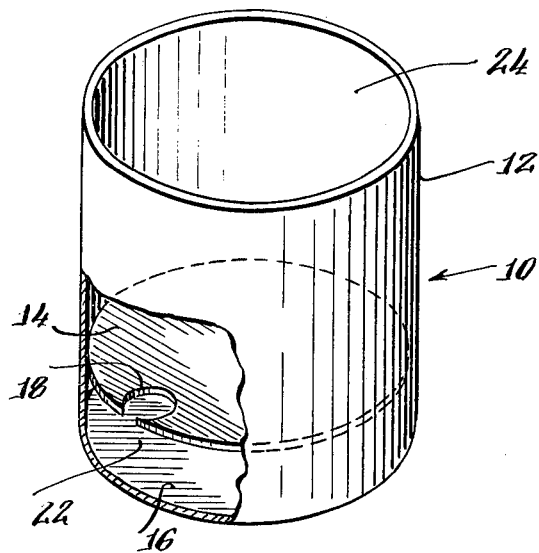
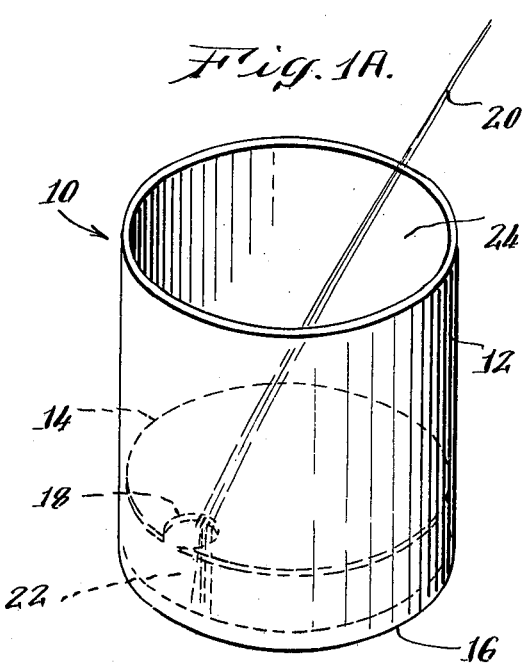
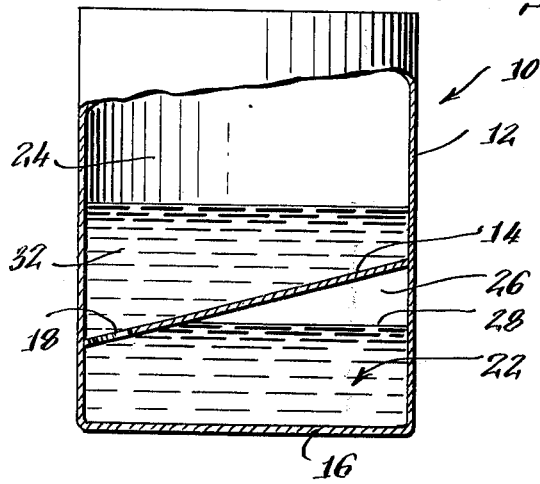
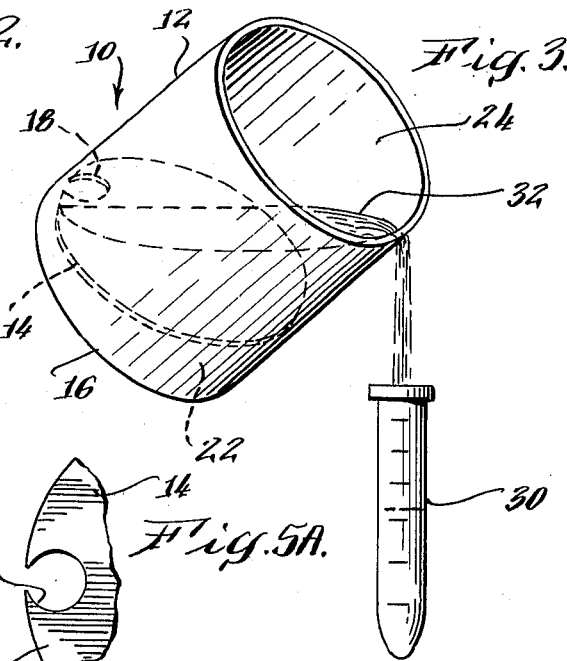
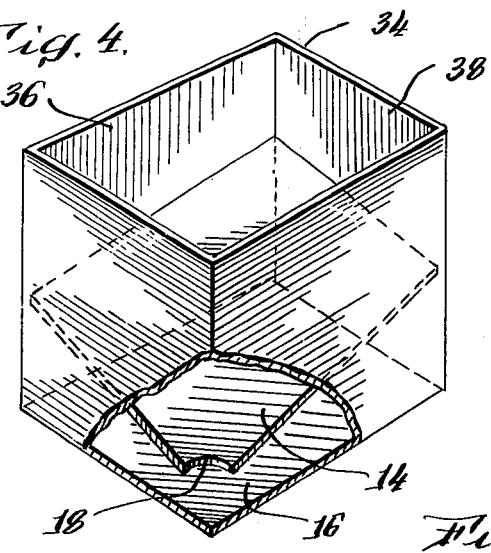
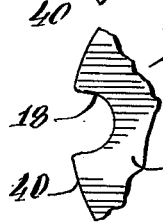
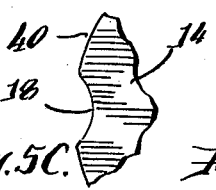

RECEPTACLE FOR COLLECTING URINE SAMPLES

BACKGROUND OF THE INVENTION

In the field of medical testing, samples of liquids, such as urine, frequently are tested. The results of such tests reflect the condition of the sample tested, which may or may not be representative of the sample taken, or of the material being produced by the patient. Various attempts have been made to render the sample tested as nearly as possible representative of the sample taken. With substances such as urine, this may be complicated by the fact that the distribution of urine may differ chemically at different locations within the bladder. Thus, heavier materials may settle to the bottom of the bladder, particularly with a quiescent patient, so that test results based on the first urine to be discharged can be quite misleading.

Various attempts have been made to overcome such difficulties, including the so-called "Mid-stream Catch" apparatus and techniques. Typically, however, they are messy, not infrequently because patients cannot exercise the necessary degree of bladder control, and often lead to test inaccuracies because of contamination from hands, receptacles, etc.

Accordingly, it is an object of this invention to provide a liquid test receptacle which is structurally simple and is effective to segregate initial portions of the sample taken from later portions.

SUMMARY OF INVENTION

Desired objectives may be achieved through practice of the present invention which, in one embodiment, comprises a receptacle having a false bottom with an aperture therethrough which includes a portion at least of the edge of said false bottom. In another embodiment, the false bottom is sloped, and the aperture is positioned at the bottom of the slope.

DESCRIPTION OF DRAWINGS

This invention may be understood from the description which follows and from the attached drawings in which FIG. 1 is a perspective view of an embodiment of the invention, FIG. 1A depicts the embodiment of this invention shown in FIG. 1 in use, FIG. 2 is a perspective view of another embodiment of this invention, FIG. 3 depicts the embodiment of the invention shown in FIG. 2, FIG. 4 is a perspective view of another embodiment of this invention, and FIGS. 5A–5F depict various representative aperture configurations useful in practice of this invention.

DESCRIPTION OF PREFERRED EMBODIMENTS

Referring first to FIG. 1, there is depicted a receptacle 10 which embodies the present invention. As shown, it is substantially cylindrical in cross-section, but as will be apparent, it may be of elliptical, or other geometry which is of curved cross-section, or of any of a number of polylaterals, such as square, rectangular, trapezoidal, hexagonal, etc. Desirably, embodiments of this invention may be made from plastic, paper, or other material which is chemically inert to the materials to which it is to be exposed, and preferably is transparent or at least transluscent for improved observation. The embodiment shown in FIG. 1 includes a side wall 12, a false bottom 14, and a true bottom 16. The false bottom 14 includes an aperture 18 therethrough. Two things in particular should be noted about the aperture 18: it is positioned at one side of the false bottom 14, and the interior of the aperture forms at least a part of the edge of the false bottom. Thus, as is shown in FIG. 1, the aperture 18 is substantially circular in shape, but the edge of the false bottom if it were present in the region where the aperture is located, would pass through the aperture. However, because of the presence of the aperture at this location, there is a break in the continuity of the false bottom edge and, in effect, the interior of the aperture forms a part, at least, of the edge of the false bottom 14. This means that where otherwise there would be a rim of some width between the aperture and the edge of the false bottom, there is none, at least for some distance, and this ensures that when the receptacle is used as hereinafter described, none of the material initially introduced into the receptacle will be retained by such a ledge, and the sample therefore will be less varied by virtue of the admixture therewith of initial material.

Fig. 1A illustrates the embodiment shown in FIG. 1 as it may be used, for example, to collect a urine sample. As shown, a stream of urine 20 is directed into the receptacle so that it hits the false bottom 14 and, by virtue of the receptacle being held so that the false bottom 14 is at least horizontal or preferably sloped to the horizontal so that the aperture 18 is at the bottom of the slope, the urine will pass through the aperture 18 into the space 22 between the false bottom 14 and the true bottom 16, until the space 22 is filled, following which the space 24 above the false bottom 14 will begin to fill up. Thus, in effect, the initial portion of the flow is effectively segregated from the remainder of the flow.

FIG. 2 illustrates another embodiment of this invention, designed to better ensure that all of the initial flow will pass into the space 22 beneath the false bottom 14 by assuring that the false bottom 14 is sloped downward toward the aperture even though the receptacle 10 is held upright; i.e., not tipped. This is achieved, as shown, by sloping the false bottom downward toward its aperture side with respect to the true bottom 16. It should be noted that this might cause some air 26 to be trapped between the top surface 28 of the liquid occupying the space 22 and the underside of the false bottom 14, but that when the receptacle is tipped, as is shown in FIG. 3, to pour liquid into another vessel, such as a centrifuge tube 30, the entrapped air 26 will bubble up through the aperture 18 and the liquid 32 positioned above the false bottom 14 and will immediately be replaced by such liquid 32 without any significant amount of admixture therewith by liquid 22. It will also be apparent from FIG. 3, that during such a pouring operation, the false floor 14 acts as a barrier to the passage of liquid 22, thus assuring that the sample so taken contains no significant portion from the liquid 22 initially placed in the receptacle. Thus, the test sample so taken, if of urine, for example, will be substantially free from any concentration of material peculiar to the initial portion of the total specimen, and will be more nearly representative without the pressure of heavier constituents which might have become concentrated gravitationally.

FIG. 4 illustrates another embodiment of this invention, in this instance a polylateral, with a square or rectangular cross-section, and with the false floor 14 sloped so that the aperture 18 positioned at one of its corners will be at the bottom of the slope where the false floor 14 is closest to the true floor 16. In this embodiment, the corner 34 at the juncture of the two sides 36, 38 may advantageously be used as a pouring spout.

FIGS. 5A through 5F inclusive illustrates various false floor-aperture configurations useful in carrying out the present invention. As illustrated, they range from arcuate apertures 18 positioned at varying degrees of depth with respect to the edge 40 of the associated arcuate false floor 14 (FIGS. 5A–5C), to apertures so shaped so positioned with respect to the edges of a polylateral false floor (FIGS. 5D and 5E), to polylateral apertures so positioned with respect to a polylateral false floor (FIG. F). Of course, these are merely to demonstrate the wide variety of configurations which may be utilized pursuant to this invention, and we by no means intended to imply that the invention is limited to the exact configurations illustrated.

Thus, it is to be understood that the embodiments shown and described are by way of illustration and not of limitation, and that a wide variety of other embodiments may be made without departing from the spirit or scope of this invention.

I claim:

1. A receptacle useful for collecting urine samples for liquids comprising a wall, a true bottom which joins and is substantially perpendicular to said wall, and a false bottom which joins said wall and has an aperture therethrough at least a portion of the perimeter of said aperture, wherein comprises a portion at least of the edge of said false bottom, and wherein said false bottom is sloped with respect to the true floor of said receptacle and said aperture is located in the region of said false bottom closest to said true floor.

2. The device described in claim 1 wherein the interior of said receptacle is round in shape.

3. The device described in claim 1 wherein the interior of said receptacle is polylateral in shape.

* * * * *